US006964855B2

(12) United States Patent
O'Connor, Jr. et al.

(10) Patent No.: US 6,964,855 B2
(45) Date of Patent: Nov. 15, 2005

(54) **PEPTIDES FOR DETECTION TO *ANAPLASMA PHAGOCYTOPHILUM***

(75) Inventors: Thomas Patrick O'Connor, Jr., Westbrook, ME (US); Ramaswamy Chandrashekar, Scarborough, ME (US)

(73) Assignee: IDEXX Laboratories, Westbrook, ME (US)

( * ) Notice: Subject to any disclaimer, the term of this patent is extended or adjusted under 35 U.S.C. 154(b) by 70 days.

(21) Appl. No.: 10/404,626

(22) Filed: Apr. 1, 2003

(65) Prior Publication Data

US 2003/0194757 A1 Oct. 16, 2003

Related U.S. Application Data

(63) Continuation-in-part of application No. 10/121,799, filed on Apr. 12, 2002, now abandoned.

(51) Int. Cl.[7] ..................... G01N 35/554; C12P 21/06; C12N 5/08; A61K 39/00; A61K 39/02
(52) U.S. Cl. ................. 435/7.32; 435/69.1; 435/366; 424/184.1; 424/234.1
(58) Field of Search ................ 435/7.32, 69.1, 435/366, 252.3, 320.1, 6, 69.3, 24.33, 243, 252.1, 260; 536/23.7, 32, 24.31–33; 530/387.1, 300, 360, 380, 827, 388.4; 424/190.1, 191, 136.1, 185, 234.1, 184.1; 514/44

(56) References Cited

U.S. PATENT DOCUMENTS

| | | | |
|---|---|---|---|
| 5,192,679 A | 3/1993 | Dawson et al. | |
| 5,401,656 A | 3/1995 | Dawson et al. | |
| 5,413,931 A | 5/1995 | Dawson et al. | |
| 5,726,010 A | 3/1998 | Clark | |
| 5,789,176 A | 8/1998 | Dawson et al. | |
| 5,869,335 A | 2/1999 | Munderloh et al. | |
| 5,928,879 A | 7/1999 | Dumler et al. | |
| 5,955,359 A | 9/1999 | Dumler et al. | |
| 5,976,791 A | 11/1999 | Mabilat et al. | |
| 5,976,860 A | 11/1999 | Coughlin et al. | |
| 5,989,848 A | 11/1999 | Dawson | |
| 6,015,691 A | 1/2000 | Walker et al. | |
| 6,025,338 A | 2/2000 | Barbet et al. | |
| 6,034,085 A | 3/2000 | Joshi et al. | |
| 6,204,252 B1 * | 3/2001 | Murphy et al. | ............... 514/44 |
| 6,207,169 B1 | 3/2001 | Reed et al. | |
| 6,231,869 B1 | 5/2001 | Reed et al. | |
| 6,277,381 B1 * | 8/2001 | Reed et al. | ............. 424/234.1 |
| 6,284,238 B1 | 9/2001 | Coughlin et al. | |
| 6,306,394 B1 | 10/2001 | Murphy et al. | |
| 6,306,402 B1 | 10/2001 | Reed et al. | |
| 6,355,777 B1 | 3/2002 | Walker et al. | |
| 6,392,023 B1 | 5/2002 | Walker et al. | |
| 6,403,780 B1 | 6/2002 | Walker et al. | |
| 6,458,942 B1 | 10/2002 | Walker et al. | |
| 2002/0064531 A1 | 5/2002 | Walker et al. | |
| 2002/0064535 A1 * | 5/2002 | Reed et al. | ............. 424/234.1 |
| 2002/0068343 A1 | 6/2002 | Reed et al. | |
| 2002/0086984 A1 | 7/2002 | Reed et al. | |
| 2002/0115840 A1 | 8/2002 | Walker et al. | |
| 2002/0132789 A1 | 9/2002 | Barbet et al. | |

FOREIGN PATENT DOCUMENTS

WO 9642740 3/1998

OTHER PUBLICATIONS

Asanovich, KM, et al. Particial Characterization of Cloned Genes Encoding Immunoreactive Proteins of *Ehrlichia equi* and the agent of Human Granulocytic Ehrlichiosis. 1996. Ab. Gen. Meet. American Society for Microbiology. Abstract No. D–22, p. 245.*

Murphy, C.I., et al. Major Antigenic Proteins of Human Granulocytic Ehrlichiosis are Encoded by Members of a Multigene Family. 1998. Infection and Immunity. vol. 66, No. 8, pp. 3715–3717.*

Lodes, M.J., et al. Serodiagnosis of Human Granulocytic Ehrlichiosis by Using Novel Combinations of Immunoreactive Recombinant proteins. 2001. Journal of Clinical Microbiology. vol. 39, No. 7, pp. 2471–2473.*

Wormser, G.P., et al. False–Positive Lyme Disease Serology in Human Granulocytic Ehrlichiosis. 1996. Lancet 347, pp. 981–982.*

Magnarelli, L.A. Coexistence of Antibodies to Tick–Borne Pathogens of Babesiosis, Ehrlichiosis, and Lyme Borreliosis in Human Sera. 1995. Journal of Clinical Microrobiology vol. 33, No. 11, pp. 3054–3057.*

McBride, et al., "*Molecular Cloning of the Gene for a Conserved Major Immunoreactive 28–Kilodalton Protein of Ehrlichia canis: a Potential Serodiagnostic Antigen*", Clinical and Diagnostic Laboratory Immunology, 6:392–399 (1999).

McBride, et al., "*A Conserved, Transcriptionally Action p28 Multigene Locus of Ehrlichia canis*", Gene 254:245–252 (2000).

Murphy et al. "*Major antigenic proteins of the agent of human granulocytic ehrlichiosis are encoded by members of a multigene family*" Infection and Immunity, 66(8):3711–3781 (1998).

Ohashi, et al., "*Cloning and Characterization of Multigenes Encoding the Immunodominant 30–Kilodalton Major Outer Membrane Proteins of Ehrlichia canis and Application of the Recombinant Protein for Serodiagnosis*", Journal of Clinical Microbiology, 36:2671–2680 (1998).

(Continued)

*Primary Examiner*—Lynette R. F. Smith
*Assistant Examiner*—Vanessa L. Ford
(74) *Attorney, Agent, or Firm*—McDonnell Boehnen Hulbert & Berghoff LLP

(57) ABSTRACT

The invention provides compositions and methods for the detection and quantification of *A. phagocytophilum* (formerly known as *Ehrlichia equi*) antibodies and antibody fragments.

23 Claims, No Drawings

OTHER PUBLICATIONS

Ohashi, et al., "*Immunodominant Major Outer Membrane Proteins of Ehrlichia chaffeensis are Encoded by a Polymorphic Multigene Family*", Infection and Immunity, 66:132–139 (1998).

Suksawat, et al., "*Seroprevalence of Ehrlichia Canis, Ehrlichia Equi and Ehrlichia Risticii in Sick Dogs from North Carolina and Virginia*", Journal Vet. Internal. Med. 14:50 (2000).

Yu, et al., "*Comparison of Ehrlichia chaffeensis Recombinant Proteins for Serologic Diagnosis of Human Monocytotropic Ehrlichiosis*", Journal of Clinical Microbiology, 37:2568–2575 (1999).

Yu, et al., "*Genetic Diverstiy of the 28–Kilodalton Outer Membrane Protein Gene in Human Isolates of Ehrlichia chaffeensis*", Journal of Clinical Microbiology, 37:1137–1143 (1999).

Yu, et al., "*Characterization of the Complete Transcriptionally Active Ehrlichia chaffeensis 28 kDa Outer Membrane Protein Multigene Family*", Gene 248:59–68 (2000).

International Search Report dated Aug. 3, 2004 for PCT/US03/10131.

Murphy, et al., "*Major Antigenic Proteins of the Agent of Human Granulocytic Ehrlichiosis Are Encoded by Members of a Multigene Familey*", Infection and Immunity, vol. 66, No. 8, p. 3711–3718, 1998.

Lodes, et al. "*Serodiagnosis of Human Granulocytic Ehrlichiosis by Using Novel Combinations of Immunoreactive Reconbinant Proteins*" Journal of Clinical Microbiology, vol. 39, No. 7, p. 2466–2476, 2001.

* cited by examiner

SEQUENCE LISTING

```
<160> NUMBER OF SEQ ID NOS: 3

<210> SEQ ID NO 1
<211> LENGTH: 26
<212> TYPE: PRT
<213> ORGANISM: Anaplasma phagocytophila
<220> FEATURE:
<221> NAME/KEY: MISC_FEATURE
<223> OTHER INFORMATION: Peptide corresponding to amino acid 74 to 99.

<400> SEQUENCE: 1

Lys Asp Gly Lys Ser Val Lys Leu Glu Ser His Lys Phe Asp Trp Asn
1               5                   10                  15

Thr Pro Asp Pro Arg Ile Gly Phe Lys Asp
            20                  25

<210> SEQ ID NO 2
<211> LENGTH: 28
<212> TYPE: PRT
<213> ORGANISM: Anaplasma phagocytophila
<220> FEATURE:
<221> NAME/KEY: MISC_FEATURE
<223> OTHER INFORMATION: Peptide corresponding to amino acid 65 to 92.

<400> SEQUENCE: 2

Glu Thr Lys Ala Val Tyr Pro Tyr Leu Lys Asp Gly Lys Ser Val Lys
1               5                   10                  15

Leu Glu Ser His Lys Phe Asp Trp Asn Thr Pro Asp
            20                  25

<210> SEQ ID NO 3
<211> LENGTH: 20
<212> TYPE: PRT
<213> ORGANISM: Anaplasma phagocytophila
<220> FEATURE:
<221> NAME/KEY: MISC_FEATURE
<223> OTHER INFORMATION: Peptide corresponding to amino acid 120 to 139

<400> SEQUENCE: 3

Leu Glu Ile Gly Tyr Glu Arg Phe Lys Thr Lys Gly Ile Arg Asp Ser
1               5                   10                  15

Gly Ser Lys Glu
            20
```

PEPTIDES FOR DETECTION TO ANAPLASMA PHAGOCYTOPHILUM

CROSS REFERENCE TO RELATED APPLICATION

This application is a continuation-in-part of U.S. patent application Ser. No. 10/121,799 filed Apr. 12, 2002, now abandoned.

FIELD OF THE INVENTION

The invention relates to methods and compositions for the detection and quantification of *Anaplasma phagocytophilum* antibodies and antibody fragments. *A. phagocytophilum* is formerly known as *Ehrlichia equi*.

BACKGROUND OF THE INVENTION

Granulocytic ehrlichiosis occurs in mammals such as humans, horses, dogs and cats and is caused by infection of granulocytic cells with the tick-borne agent *Anaplasma phagocytophilum* (formerly known as *Ehrichia equi*). Frequently reported symptoms of granulocytic ehrlichiosis in humans are leukopenia and thrombocytopenia. Common clinical signs in dogs and horses are fever and anexoria.

Indirect immunofluorescence assays (IFA) and enzyme-linked immunosorbent assays (ELISA) are frequently used as aids in the diagnosis of diseases caused by *A. phagocytophilum* by measuring the binding of antibody from a patient's blood or serum to infected cells, cell lysates or purified ehrlichial proteins. However, these assays are severely limited in usefulness because of sensitivity and specificity issues directly related to the impure nature of the antigen used in these tests. Highly purified reagents are needed to construct more accurate assays. This invention discloses specific synthetic peptide sequences derived from *A. phagocytophilum* that can be used in place of partially purified proteins, infected cells or cell lysates.

SUMMARY OF THE INVENTION

It is an object of the invention to provide methods and compositions for the detection and quantification of *A. phagocytophilum* antibodies and antibody fragments. This and other objects of the invention are provided by one or more of the embodiments described below.

One embodiment of the invention provides a composition of matter consisting essentially of an isolated polypeptide shown in SEQ ID NO:1, SEQ ID NO:2, or SEQ ID NO:3. The composition can comprise a carrier. The isolated polypeptide of the composition can be conjugated to bovine serum albumin. The polypeptide of the composition can consist essentially of a fragment of at least about 5 contiguous amino acids of SEQ ID NO:1, SEQ ID NO:2, or SEQ ID NO:3. The invention also comprises an isolated polynucleotide encoding the isolated polypeptide of the composition.

Another embodiment of the invention provides a method of detecting antibodies specific for *A. phagocytophilum*. The method comprises contacting a polypeptide shown in SEQ ID NO:1, SEQ ID NO:2, SEQ ID NO:3, or a combination of two or three polypeptides SEQ ID NO:1, SEQ ID NO:2, and SEQ ID NO:3 with a test sample suspected of comprising antibodies that are specific for *A. phagocytophilum*, under conditions that allow polypeptide/antibody complexes to form. The polypeptide can be attached to a substrate and can be in a multimeric form. The test sample can a biological sample obtained from a mammal, such as a human, cat, horse or dog. Polypeptide/antibody complexes are detected. The detection of polypeptide/antibody complexes is an indication that antibodies specific for *A. phagocytophilum* are present in the test sample. The polypeptide/antibody complexes can be contacted with an indicator reagent comprising a signal generating compound prior to the detection step. The antibodies can be antibody fragments. The amount of antibody in a test sample can be determined using this method. The method can comprise an assay selected from the group of assays consisting of a reversible flow chromatographic binding assay, an enzyme linked immunosorbent assay, a radioimmunoassay, a hemagglutination assay a western blot assay, a fluorescence polarization immunoassay and an indirect immunofluorescence assay.

Still another embodiment of the invention comprises an article of manufacture comprising packaging material and, contained within the packaging material, a polypeptide shown in SEQ ID NO:1, SEQ ID NO:2, or SEQ ID NO:3, or a combination of two or three polypeptides shown in SEQ ID NO:1, SEQ ID NO:2, and SEQ ID NO:3. The packaging material can comprise a label that indicates that the one or more polypeptides can be used for the identification of *A. phagocytophilum* infection in a mammal.

Even another embodiment of the invention provides a method of diagnosing an *A. phagocytophilum* infection in a mammal. The method comprises obtaining a biological sample from a mammal suspected of having an *A. phagocytophilum* infection and contacting a polypeptide shown in SEQ ID NO:1, SEQ ID NO:2, or SEQ ID NO:3 or a combination of two or three polypeptides SEQ ID NO:1, SEQ ID NO:2 and SEQ ID NO:3, with the biological sample under conditions that allow polypeptide/antibody complexes to form. The polypeptide/antibody complexes are detected. The detection of polypeptide/antibody complexes is an indication that the mammal has an *A. phagocytophilum* infection. The polypeptide/antibody complexes can be contacted with an indicator reagent comprising a signal generating compound prior to the detection step. The mammal can be a human, cat, horse or dog.

Another embodiment of the invention provides an antibody that specifically binds to at least one epitope of an *A. phagocytophilum* polypeptide, wherein said polypeptide is SEQ ID NO:1, SEQ ID NQ:2 or SEQ ID NO:3. The antibody can be a monoclonal antibody.

The invention therefore provides methods and compositions that can be used to detect *A. phagocytophilum* antibodies and antibody fragments with improved sensitivity and specificity.

DETAILED DESCRIPTION OF THE INVENTION

Immunodominant regions of a P30 protein of *E. canis* have previously been identified using phage display technology. See U.S. patent application Ser. No. 09/765,736 filed Jan. 18, 2001. The identified sequences exhibited strong homology to sequences for outer membrane proteins of several isolates of *Ehrlichia canis*. Synthetic peptides corresponding to sequences from homologous regions of several outer membrane proteins have been synthesized and used in diagnostic assays to detect antibodies and antibody fragments to *E. canis*.

*A. phagocytophilum* and *E. canis* are different species of related organisms that are classified within different serotypes of the *Ehrlichia* group. Polypeptide sequences of *A. phagocytophilum* were examined to identify immunodominant regions. Immunodominant sequences derived from an A. phagocytophilum membrane protein, GE E8 msp-2, were identified by comparison to E. canis immunodominant polypeptides (Murphy et al., Infection and Immunity, vol. 66(8), pp. 3711–3718 (1998)). The following sequences, which correspond to amino acids numbers 74 to 99, 62 to 92 and 20–39 of an *A. phagocytophilum* membrane protein, were identified and used as a basis to synthesize three synthetic peptides:

```
Peptide I. Amino Acid Nos. 74–99
K D G K S V K L E S H K F D W N T P D P R I G F K D        (SEQ ID NO:1)

Peptide II. Amino Acid Nos. 65–92
E T K A V Y P Y L K D G K S V K L E S H K F D W N T P D    (SEQ ID NO:2)

Peptide III. Amino Acid Nos. 20–39
L E I G Y E R F K T K G I R D S G S K E                    (SEQ ID NO:3)
```

*A. phagocytophilum* Polypeptides

In one embodiment of the invention, a polypeptide or fragment thereof is substantially pure. Substantially pure means that a polypeptide of the invention is substantially free from other biological molecules. A substantially pure polypeptide is at least 75%, 80%, 90%, 95%, 97%, 99% or 100% pure by dry weight. Purity can be measured by a method such as column chromatography, polyacrylamide gel electrophoresis, or HPLC analysis.

Polypeptides of the invention can also comprise fragments of the polypeptides shown in SEQ ID NO:1, SEQ ID NO:2, and SEQ ID NO:3. For example, fragments of polypeptides can comprise at least about 5, 6, 8, 10, 12, 15, 18, 20, 22, 24, or 26 contiguous amino acids of the polypeptides shown in SEQ ID NO:1, SEQ ID NO:2, or SEQ ID NO:3.

Polypeptides of the invention can also comprise conservative variants of the polypeptides shown in SEQ ID NO:1, SEQ ID NO:2, and SEQ ID NO:3. A conservative variant is a polypeptide that differs from SEQ ID NO:1, SEQ ID NQ:2, or SEQ ID NO:3, or a fragment thereof, only in conservative substitutions, such that the antigenic properties of the polypeptide are substantially the same as the original polypeptide. Conservative variants can generally be identified by modifying a polypeptide sequence of the invention and evaluating the antigenic activity of the modified polypeptide using, for example, an immunohistochemical assay, an enzyme-linked immunosorbant assay (ELISA), a radioimmunoassay (RIA), or a western blot assay. A variant, including a conservative variant and an antigenically active variant will bind to an anti-*A. phagocytophilum* antibody or antibody fragment with substantially the same binding specificity of a polypeptide shown in SEQ ID NO; 1, SEQ ID NO:2, or SEQ ID NO:3. "Binding specificity" or "specifically binds" means that a polypeptide will substantially recognize and bind to an anti-*A. phagocytophilum* polyclonal or monoclonal antibody or antibody fragment (e.g., a Fv, single chain Fv, Fab', or F(ab')2 fragment), but does not substantially bind to other molecules in a test sample. Specific binding can be tested using, e.g, an immunohistochemical assay, an enzyme-linked immunosorbant assay (ELISA), a radioimmunoassay (RIA), or a western blot assay. Polypeptides of the invention can comprise up to about 1, 2, 3, 5, 6, 10, or 15 conservative amino acid substitutions.

A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. That is, amino acids within each of the groups can be substituted for another amino acid of the same group.

A polypeptide of the invention or fragments thereof can differ from the corresponding sequence in SEQ ID NO:1, SEQ ID NO:2, or SEQ ID NO:3 and yet retain substantially the same antigenic activity of the original polypeptide or fragment. This is an antigenically active variant or an antigenically active fragment. A conservative variant is one type of an antigenically active variant or fragment. Naturally occurring antigenically active variants, such as allelic variants and non-naturally occurring antigenically active variants, are included in the invention and can be produced by, for example, mutagenesis techniques or by direct synthesis.

An antigenically active variant differs by about, for example, 1, 2, 3, 5, 6, 10, 15 or 20 amino acid residues from a polypeptide shown in SEQ ID NO:1, SEQ ID NO:2, or SEQ ID NO:3 or a fragment thereof. Where this comparison requires alignment the sequences are aligned for maximum homology. Deletions, insertions, substitutions, repeats, inversions or mismatches are considered differences. The differences are, preferably, differences or changes at a non-essential residue or a conservative substitution. The site of variation can occur anywhere in the polypeptide, as long as the resulting variant polypeptide is antigenicity substantially similar to a polypeptide shown in SEQ ID NO:1, SEQ ID NO:2, or SEQ ID NO:3.

A polypeptide is an antigenically active variant or antigenically active fragment if it reacts substantially the same as a polypeptide shown in SEQ ID NO:1, SEQ ID NO:2, or SEQ ID NO:3 in an assay such as an immunohistochemical assay, an ELISA, an RIA, an IFA, or a western blot assay, e.g. has about 90–110% of the activity of the original polypeptide. In one embodiment, the assay is a competition assay wherein the antigenically active variant polypeptide or fragment is capable of reducing binding of a polypeptide shown in SEQ ID NO:1, SEQ ID NO:2, or SEQ ID NO:3 to a corresponding reactive antigen or antibody by about 90, 95, 99, or 100%.

Therefore, the invention provides antigenically active variant polypeptides that can be at least 85% identical, more preferably at least 90% identical, and still more preferably at least 95%, 96%, 97%, 98%, or 99% identical to a polypeptide sequence shown in SEQ ID NO:1, SEQ ID NO:2, or SEQ ID NO:3.

Identity or identical means amino acid sequence similarity and has an art recognized meaning. Sequences with identity share identical or similar amino acids, where similar amino acids are preferably conserved amino acids. Thus, a candidate sequence sharing 90% amino acid sequence identity with a reference sequence (i.e., SEQ ID NO:1) requires that, following alignment of the candidate sequence with the reference sequence, 90% of the amino acids in the candidate sequence are identical to the corresponding amino acids in the reference sequence, and/or constitute conservative amino acid changes.

Sequences are aligned for identity calculations using a mathematical algorithm, such as the algorithm of Karlin and Altschul (1990) *Proc. Natl. Acad. Sci. USA* 87:2264–2268, modified as in Karlin and Altschul (1993) *Proc. Natl. Acad. Sci. USA* 90:5873–5877. Such an algorithm is incorporated into the XBLAST programs of Altschul et al. (1990) *J. Mol. Biol.* 215:403–410. BLAST protein searches can be performed with the XBLAST program, score=50, wordlength=3 to obtain amino acid sequences with identity to the polypeptides of the invention. To obtain gapped alignments for comparison purposes, Gapped BLAST can be utilized as described in Altschul et al. (1997) *Nucleic Acids Res.* 25:3389–3402. When utilizing BLAST and Gapped BLAST programs, the default parameters of the respective programs (e.g., XBLAST) can be used. Internal gaps and amino acid insertions in the candidate sequence as aligned are ignored when making the identity calculation.

Methods of introducing a mutation into amino acids of a protein is well known to those skilled in the art. See, e.g., Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989). Mutations can also be introduced using commercially available kits such as "QUIKCHANGE™ Site-Directed Mutagenesis Kit" (Stratagene). The generation of a polypeptide antigenically substantially equivalent to a polypeptide shown in SEQ ID NO:1, SEQ ID NO:2, or SEQ ID NO:3 by replacing an amino acid that does not influence the antigenicity of a polypeptide of the invention can be accomplished by one skilled in the art.

Polypeptides of the invention comprise at least one epitope that is recognized by an anti-*A. phagocytophila* antibody or fragment. An epitope is an antigenic determinant of a polypeptide. An epitope can be a linear, sequential, or conformational epitope. Epitopes within a polypeptide of the invention can be identified by several methods. See, e.g., U.S. Pat. No. 4,554,101; Jameson & Wolf, *CABIOS* 4:181–186 (1988). For example, a polypeptide of the invention can be isolated and screened. A series of short peptides, which together span the entire polypeptide sequence, can be prepared by proteolytic cleavage. By starting with, for example, 20-mer polypeptide fragments, each fragment can be tested for the presence of epitopes recognized in, for example, an enzyme-linked immunosorbent assay (ELISA). In an ELISA assay a polypeptide, such as a 20-mer polypeptide fragment, is attached to a solid support, such as the wells of a plastic multi-well plate. A population of antibodies or antibody fragments are labeled, added to the solid support and allowed to bind to the unlabeled antigen, under conditions where non-specific adsorbtion is blocked, and any unbound antibody and other proteins are washed away. Antibody binding is detected by, for example, a reaction that converts a colorless indicator reagent into a colored reaction product. Progressively smaller and overlapping fragments can then be tested from an identified 20-mer to map the epitope of interest.

Preferably, a polypeptide of the invention is synthesized using conventional peptide synthesizers, which are well known in the art. A polypeptide of the invention can also be produced recombinantly. A polynucleotide encoding an *A. phagocytophilum* polypeptide can be introduced into an expression vector that can be expressed in a suitable expression system using techniques well known in the art. A variety of bacterial, yeast, plant, mammalian, and insect expression systems are available in the art and any such expression system can be used. Optionally, a polynucleotide encoding an *A. phagocyphilum* polypeptide can be translated in a cell-free translation system.

A polypeptide of the invention can be produced as a fusion protein that contains other amino acid sequences, such as amino acid linkers or signal sequences, as well as ligands useful in protein purification, such as glutathione-S-transferase, histidine tag, and staphylococcal protein A. More than one polypeptide of the invention can be present in a fusion protein. The polypeptide can be fused to the N-terminus or C-terminus of a polypeptide of the invention.

A polypeptide of the invention can be synthesized such that it comprises several repeated *A. phagocytophilum* polypeptides. This is a multimeric polypeptide. These repeated polypeptides can comprise one specific polypeptide, e.g. the polypeptide shown in SEQ ID NO:1, repeated 2 or more times. Alternatively, the repeated polypeptides can comprise one or more copies of an *A. phagocytophilum* polypeptide. For example, such polypeptides can comprise one or more copies of an *A. phagocytophilum* polypeptide shown in SEQ ID NO:1 along with one or more copies of an *A. phagocytophilum* polypeptide shown in SEQ ID NO:2 and/or SEQ ID NO:3. A polypeptide of the invention can be combined or synthesized with one or more non-*A. phagocytophilum* polypeptides, fragments of polypeptides, or full-length polypeptides.

A polypeptide of the invention can be combined with a carrier. A carrier is a vehicle for a polypeptide of the invention. Carriers include, for example, excipients, diluents, adjuvants, and stabilizers. Examples of such stabilizers are proteins such as serum albumins and gelatin; saccharides such as glucose, sucrose, lactose, maltose, trehalose, sorbitol, maltitol, mannitol and lactitol; and buffers which are mainly composed of phosphate or succinate.

*A. phagoptophilum* Polynucleotides

Polynucleotides of the invention contain less than an entire microbial genome and can be RNA or single- or double-stranded DNA. Preferably, the polynucleotides are purified free of other components, such as proteins and lipids. The polynucleotides of the invention encode the polypeptides described above. Polynucleotides of the invention can also comprise other nucleotide sequences, such as sequences coding for linkers, signal sequences, heterologous signal sequences, TMR stop transfer sequences, transmembrane domains, or ligands useful in protein purification such as glutathione-S-transferase, histidine tag, and staphylococcal protein A.

Polynucleotides can be synthesized in the laboratory, for example, using an automatic synthesizer. An amplification method such as PCR can be used to amplify polynucleotides from either genomic DNA or cDNA encoding the polypeptides.

If desired, polynucleotides can be cloned into an expression vector comprising, for example, promoters, enhancers, or other regulatory elements that drive expression of the polynucleotides of the invention in host cells. An expression vector can be, for example, a plasmid, such as pBR322, pUC, or ColE1, or an adenovirus vector, such as an adenovirus Type 2 vector or Type 5 vector.

A vector comprising a polynucleotide of the invention can be transformed into, for example, bacterial, yeast, insect, or mammalian cells so that the polypeptides of the invention can be expressed in and isolated from cell culture. Any techniques that are known and available in the art can be used to introduce polynucleotides into the host cells. These include, but are not limited to, transfection with naked or encapsulated nucleic acids, cellular fusion, protoplast fusion, viral infection, and electroporation.

Polynucleotides of the invention can be used to produce polypeptides of the invention and, for example, as probes or primers to detect the presence of *A. phagocytophilum* polynucleotides in a sample, such as a biological sample. The ability of such probes to specifically hybridize to *A. phagocytophilum* polynucleotide sequences will enable them to be of use in detecting the presence of complementaiy sequences in a given sample.

Methods of Detection

The methods of the invention can be used to detect antibodies or antibody fragments specific for *A. phagocytophilum* in a test sample, such as a biological sample, an environmental sample, or a laboratory sample. A biological sample can include, for example, sera, blood, cells, plasma, or tissue from a mammal such as a horse, cat, dog or human. The test sample can be untreated, precipitated, fractionated, separated, diluted, concentrated, or purified before combining with a polypeptide of the invention.

The methods comprise contacting a polypeptide of the invention with a test sample under conditions that allow a polypeptide/antibody complex to form. That is, a polypeptide of the invention specifically binds to an antibody specific for *A. phagocytophilum* located in the sample. The formation of a complex between the polypeptide and anti-*A. phagocytophilum* antibodies in the sample is detected. In one embodiment of the invention, the polypeptide/antibody complex is detected when an indicator reagent, such as an enzyme, which is bound to the antibody, catalyzes a detectable reaction. Optionally, an indicator reagent comprising a signal generating compound can be applied to the polypeptide/antibody complex under conditions that allow formation of a polypeptide/antibody/indicator complex. The polypeptide/antibody/indicator complex is detected. Optionally, the polypeptide or antibody can be labeled with an indicator reagent prior to the formation of a polypeptide/antibody complex. The method can optionally comprise a positive or negative control.

Assays of the invention include, but are not limited to those based on competition, direct reaction or sandwich-type assays. Assays can use solid phases or substrates or can be performed by immunoprecipitation or any other methods that do not utilize solid phases. Where a solid phase or substrate is used, a polypeptide of the invention is directly or indirectly attached to a solid support or a substrate such as a microtiter well, magnetic bead, non-magnetic bead, column, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). A preferred substrate is sintered, fine particles of polyethylene, commonly known as porous polyethylene, for example, 10–15 micron porous polyethylene from Chromex Corporation (Albuquerque, N. Mex.). All of these substrate materials can be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like.

Polypeptides of the invention can be used to detect anti-*A. phagocytophilum* antibodies or antibody fragments in assays including, but not limited to enzyme linked immunosorbent assay (ELISA), western blot, IFA, radioimmunoassay (RIA), hemagglutination (HA), and fluorescence polarization immunoassay (FPIA). A preferred assay of the invention is the reversible flow chromatographic binding assay, for example a SNAP® assay. See U.S. Pat. No. 5,726,010.

In one type of assay format, one or more polypeptides can be coated on a solid phase or substrate. A test sample suspected of containing an anti-*A. phagocytophilum* antibody or fragment thereof is incubated with an indicator reagent comprising a signal generating compound conjugated to an antibody or antibody fragment specific for *A. phagocytophilum* for a time and under conditions sufficient to form antigen/antibody complexes of either antibodies of the test sample to the polypeptides of the solid phase or the indicator reagent compound conjugated to an antibody specific for *A. phagocytophilum* to of the solid phase. The reduction in binding of the indicator reagent conjugated to an anti-*A. phagocytophilum* antibody to the solid phase can be quantitatively measured. A measurable reduction in the signal compared to the signal generated from a confirmed negative *A. phagocytophilum* test sample indicates the presence of anti-*A. phagocytophilum* antibody in the test sample. This type of assay can quantitate the amount of anti-*A. phagocytophilum* antibodies in a test sample.

In another type of assay format, one or more polypeptides of the invention are coated onto a support or substrate. A polypeptide of the invention is conjugated to an indicator reagent and added to a test sample. This mixture is applied to the support or substrate. If *A. phagocytophilum* antibodies are present in the test sample they will bind the polypeptide conjugated to an indicator reagent and to the polypeptide immobilized on the support. The polypeptide/antibody/indicator complex can then be detected. This type of assay can quantitate the amount of anti-*A. phagocytophilum* antibodies in a test sample.

The formation of a polypeptide/antibody complex or a polypeptide/antibody/indicator complex can be detected by radiometric, colormetric, fluorometric, size-separation, or precipitation methods. Optionally, detection of a polypeptide/antibody complex is by the addition of a secondary antibody that is coupled to an indicator reagent comprising a signal generating compound. Indicator reagents comprising signal generating compounds (labels) associated with a polypeptide/antibody complex can be detected using the methods described above and include chromogenic agents, catalysts such as enzymes, fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzymes include alkaline phosphatase, horseradish peroxidase, beta-galactosidase, and the like. The selection of a particular label is not critical, but it will be capable of producing a signal either by itself or in conjunction with one or more additional substances.

Formation of the complex is indicative of the presence of anti-*A. phagocytophilum* antibodies in a test sample. Therefore, the methods of the invention can be used to diagnose *A. phagocytophilum* infection in a patient.

The methods of the invention can also indicate the amount or quantity of anti-*A. phagocytophilum* antibodies in a test sample. With many indicator reagents, such as enzymes, the amount of antibody present is proportional to the signal generated. Depending upon the type of test sample, it can be diluted with a suitable buffer reagent, concentrated, or contacted with a solid phase without any manipulation. For example, it usually is preferred to test serum or plasma samples that previously have been diluted, or concentrate specimens such as urine, in order to determine the presence and/or amount of antibody present.

The invention further comprises assay kits (e.g., articles of manufacture) for detecting anti-*A. phagocytophilum* antibodies or antibody fragments in a sample. A kit or article of manufacture comprises one or more polypeptides of the invention and means for determining binding of the polypeptide to *A. phagocytophilum* antibodies or antibody fragments in the sample. A kit can comprise a device containing one or more polypeptides of the invention and instructions for use of the one or more polypeptides for the identification of an *A. phagocytophilum* infection in a mammal. The kit can also comprise packaging material comprising a label that indicates that the one or more polypeptides of the kit can be used for the identification of *A. phagocytophilum* infection. Other components such as buffers, controls, and the like, known to those of ordinary skill in art, can be included in such test kits. The polypeptides, assays, and kits of the invention are useful, for example, in the diagnosis of individual cases of *A. phagocytophilum* infection in a patient, as well as epidemiological studies of *A. phagocytophilum* outbreaks.

Polypeptides and assays of the invention can be combined with other polypeptides or assays to detect the presence of *A. phagocytophilum* along with other organisms. For example, polypeptides and assays of the invention can be combined with reagents that detect heartworm and/or *Borrelia burgdorferi*.

Monoclonal Antibodies

The polypeptides of the invention can also be used to develop monoclonal and/or polyclonal antibodies that specifically bind to an immunological epitope of *A. phagocytophilum* present in the polypeptides of the invention.

The antibodies or fragments thereof can be employed in assay systems, such as a reversible flow chromatographic binding assay, enzyme linked immunosorbent assay, western blot assay, or indirect immunofluorescence assay, to determine the presence, if any, of *A. phagocytophilum* polypeptides or antibodies in a test sample. In addition, these antibodies, in particular monoclonal antibodies, can be bound to matrices similar to CNBr-activated Sepharose and used for the affinity purification of specific *A. phagocytophilum* proteins from, for example, cell cultures or blood serum, such as to purify recombinant and native *A. phagocytophilum* antigens and proteins. The monoclonal antibodies of the invention can also be used for the generation of chimeric antibodies for therapeutic use, or other similar applications.

Monoclonal antibodies directed against *A. phagocytophilum* epitopes can be produced by one skilled in the art. The general methodology for producing such antibodies is well-known and has been described in, for example, Kohler and Milstein, Nature 256:494 (1975) and reviewed in J. G. R. Hurrel, ed., *Monoclonal Hybridoma Antibodies: Techniques and Applications*, CRC Press Inc., Boca Raton, Fla. (1982), as well as that taught by L. T. Mimms et al., *Virology* 176:604–619 (1990). Immortal antibody-producing cell lines can be created by cell fusion, and also by other techniques such as direct transformation of B lymphocytes with oncogenic DNA, or transfection with Epstein-Barr virus.

The following are provided for exemplification purposes only and are not intended to limit the scope of the invention described in broad terms above. All references cited in this disclosure are incorporated herein by reference.

EXAMPLES

Example 1

Canine

Three *A. phagocytophilum* antibody positive and three *A. phagocytophilum* antibody negative control canine samples (confirmed by Western blot) were obtained from the Connecticut Agricultural Experiment Station (New Haven, Conn.). The positive samples were supplied with *A. phagocytophilum* antibody ELISA titers determined by the Connecticut Agricultural Experiment Station using an *A. phagocytophilum* whole cell lysate as an antigen source.

The *A. phagocytophilum* ELISA titers and results of the microtiter-plate based immunoassay were obtained using a mixture (50:50) of the synthetic peptides shown in SEQ ID NO:1 and SEQ ID NO:2. Immunoassay synthetic peptides were immobilized on microtiter wells. A dilution of the test sample was added to the microtiter well and unbound antibody was removed by washing. Antibody bound to the immobilized peptide was detected by reaction with an anti-species, in this case canine, horseradish peroxidase (HRPO) conjugate, washing and addition of a HRPO substrate. The optical density of individual microtiter wells was determined using a microtiter plate reader. The results are shown in Table 1.

Example 2

Equine

Three *A. phagocytophilum* antibody positive and three *A. phagocytophilum* antibody negative control equine samples (confirmed by Western blot) were obtained from the Connecticut Agricultural Experiment Station. The positive samples were supplied with *A. phagocytophilum* antibody ELISA titers determined by the Connecticut Agricultural Experiment Station using an *A. phagocytophilum* whole cell lysate as an antigen source. *A. phagocytophilum* ELISA titers and the results of a microtiter-plate based immunoassay were obtained using a mixture (50:50) of SEQ ID NO:1 and SEQ ID NO:2. The peptide-based assay was performed as described above using an anti-equine:HRPO conjugate. The results are shown in Table 2.

Example 3

Feline

Three *A. phagocytophilum* antibody positive and two *A. phagocytophilum* antibody negative feline samples were obtained from Dr. Steve Levy, a Connecticut veterinarian. Samples were confirmed by an immunofluorescence assay (IFA) at North Carolina State University using an *A. phagocytophilum* whole cell lysate as an antigen source.

The *A. phagocytophilum* titers determined by IFA and results of the microtiter-plate based immunoassay were obtained using a mixture (50:50) of SEQ ID NO:1 and SEQ ID) NO:2. The peptide-based assay was performed as described above using an anti-feline:HRPO conjugate. The results are shown in Table 3.

Example 4

Canine (SEQ ID NO:3)

Three *A. phagocytophilum* antibody positive and three *A. phagocytophilum* antibody negative control canine samples, confirmed by IFA, were obtained from Dr. Steve Levy.

Antibodies to SEQ ID NO:3 were determined by microtiter-plate based immunoassay. The synthetic peptide was immobilized on microtiter wells. A dilution of the test sample was added to the microtiter well and unbound antibody was removed by washing. Antibody bound to the immobilized peptide was detected by reaction with an anti-species, in this case canine, horseradish peroxidase (HRPO) conjugate, washing and addition of a HRPO substrate. The optical density of individual microtiter wells was determined using a microtiter plate reader. The results are shown in Table 4.

Example 5

Equine (SEQ ID NO:3)

Three *A. phagocytophilum* antibody positive and three *A. phagocytophilum* antibody negative control equine samples confirmed by IFA were obtained from Connecticut Veterinary Diagnostic Laboratory.

Antibodies to SEQ ID NO:3 were determined by microtiter-plate based immunoassay. The peptide-based assay was performed as described above using an anti-equine:HRPO conjugate. The results are shown in Table 5.

Example 6

Feline (SEQ ID NO:3)

Three *A. phagocytophilum* antibody positive and *A. phagocytophilum* antibody negative feline samples, confirmed by IFA, were obtained from Dr. Steve Levy.

Antibodies to SEQ ID NO:3 were determined by microtiter-plate based immunoassay. The peptide-based assay was performed as described above using an anti-feline:HRPO conjugate. The results are shown in Table 6.

TABLE 1

Comparison of ELISA results using *A. phagocytophilum* whole cell lysate as antigen source and *A. phagocytophilum* synthetic peptides.

| Sample ID | Species | *A. phagocytophilum* ELISA Titer/Result[1] | *A. phagocytophilum* Synthetic Peptides ELISA OD/Result |
|---|---|---|---|
| 2249 | Canine | 2560/Pos | 0.068/Pos |
| 2185 | Canine | 20480/Pos | 0.504/Pos |
| 2292 | Canine | 10240/Pos | 0.342/Pos |
| WY05 | Canine | Neg | 0.034/Neg |
| WY023 | Canine | Neg | 0.036/Neg |
| WY013 | Canine | Neg | 0.031/Neg |

[1]Connecticut Agricultural Experiment Station

TABLE 2

Comparison of ELISA results using *A. phagocytophilum* whole cell lysate as antigen source and *A. phagocytophilum* synthetic peptides.

| Sample ID | Species | *A. phagocytophilum* ELISA Titer/Result[1] | *A. phagocytophilum* Synthetic Peptides ELISA OD/Result |
|---|---|---|---|
| HO4a | Equine | 40960/Pos | 0.261/Pos |
| H46 | Equine | 5120/Pos | 0.48/Pos |
| H22 | Equine | 20480/Pos | 0.362/Pos |
| Kent 29 | Equine | Neg | 0.055/Neg |
| Kent 26 | Equine | Neg | 0.056/Neg |
| Kent 30 | Equine | Neg | 0.046/Neg |

[1]Connecticut Agricultural Experiment Station

TABLE 3

Comparison of IFA results using *A. phagocytophilum* whole cell lysate as antigen source and ELISA using *A. phagocytophilum* synthetic peptides

| Sample ID | Species | *A. phagocytophilum* Whole Cell Lysate IFA Titer/Result[2] | *A. phagocytophilum* Synthetic Peptides ELISA OD/Result |
|---|---|---|---|
| F8 | Feline | 2048/Pos | 0.678/Pos |
| F15 | Feline | 2048/Pos | 0.848/Pos |
| F19 | Feline | 64/Pos | 0.095/Pos |
| F2 | Feline | Neg | 0.036/Neg |
| F3 | Feline | Neg | 0.037/Neg |

[2]North Carolina State University

TABLE 4

ELISA results using *A. phagocytophilum* synthetic peptide.

| Sample ID | Species | *A. phagocytophilum* IFA | *A. phagocytophilum* Synthetic Peptide SEQ ID NO:3 ELISA OD/Result |
|---|---|---|---|
| DP87 | Canine | Pos | 0.742/Pos |
| DP46 | Canine | Pos | 0.911/Pos |
| DP20 | Canine | Pos | 1.157/Pos |
| DP81 | Canine | Neg | 0.024/Neg |
| DP88 | Canine | Neg | 0.006/Neg |
| DP31 | Canine | Neg | 0.031/Neg |

TABLE 5

ELISA results using *A. phagocytophilum* synthetic peptide.

| Sample ID | Species | *A. phagocytophilum* IFA | *A. phagocytophilum* Synthetic Peptide SEQ ID NO:3 ELISA OD/Result |
|---|---|---|---|
| 42 | Equine | Pos | 0.240/Pos |
| 535 | Equine | Pos | 0.355/Pos |
| 6 | Equine | Pos | 0.369/Pos |
| 98 | Equine | Neg | 0.041/Neg |
| 284 | Equine | Neg | 0.047/Neg |
| 315 | Equine | Neg | 0.048/Neg |

TABLE 6

ELISA results using *A. phagocytophilum* synthetic peptide.

| Sample ID | Species | *A. phagocytophilum* IFA | *A. phagocytophilum* Synthetic Peptide SEQ ID NO:3 ELISA OD/Result |
|---|---|---|---|
| CP88 | Feline | Pos | 0.250/Pos |
| CP05 | Feline | Pos | 0.150/Pos |
| CP02 | Feline | Pos | 1.050/Pos |
| CP27 | Feline | Neg | 0.045/Neg |
| CP42 | Feline | Neg | 0.043/Neg |

What is claimed is:

1. A method of detecting antibodies specific for *A. phagocytophilum* comprising:
   (a) contacting at least one polypeptide consisting essentially of SEQ ID NO:1 and SEQ ID NO:2 with a test sample suspected of comprising antibodies specific for *A. phagocytophilum*, under conditions that allow polypeptide/antibody complexes to form;
   (b) detecting polypeptide/antibody complexes;
   wherein the detection of polypeptide/antibody complexes is an indication that antibodies specific for *A. phagocytophilum* are present in the test sample.

2. The method of claim 1, further comprising contacting the complexes of step (a) with an indicator reagent comprising a signal generating compound prior to the performance of step (b).

3. The method of claim 1, wherein the antibodies are fragments of antibodies.

4. The method of claim 1, wherein the amount of the antibody in the test sample is determined.

5. The method of claim 1, wherein the at least one of the polypeptides of SEQ ID NO:1 and SEQ ID NO: 2 is attached to a substrate.

6. The method of claim 1, wherein the at least one polypeptide is SEQ ID NO:1.

7. The method of claim 1, wherein the at least one polypeptide is SEQ ID NO:2.

8. The method of claim 1, wherein the at least one polypeptide is in multimeric form.

9. The method of claim 1, wherein the at least one polypeptide of SEQ ID NO:1 and SEQ ID NO:2 is a fusion protein comprising the polypeptides of SEQ ID NO:1 and SEQ ID NO:2.

10. The method of claim 9, wherein the at least one polypeptide is in multimeric form.

11. The method of claim 1, wherein the test sample comprises a biological sample obtained from a mammal.

12. The method of claim 11, wherein the mammal is selected from the group consisting of humans, cats, horses and dogs.

13. The method of claim 1, wherein the method comprises an assay selected from the group of assays consisting of a reversible flow chromatographic binding assay, an enzyme linked immunosorbent assay, a radioimmunoassay, a hemagglutination assay, a western blot assay, a fluorescence polarization immunoassay, and an indirect immunofluorescence assay.

14. A method of diagnosing an infection in a mammal comprising:
  (a) obtaining a biological sample from a mammal suspected of having an *A. phagocytophilum* infection;
  (b) contacting at least one polypeptide consisting essentially of SEQ ID NO:1 and SEQ ID NO:2, with the biological sample from (a) under conditions that allow polypeptide/antibody complexes to form;
  (c) detecting polypeptide/antibody complexes; wherein the detection of polypeptide/antibody complexes is an indication that the mammal has an *A. phagocytophilum* infection.

15. The method of claim 14, further comprising contacting the polypeptide/antibody complexes of step (b) with an indicator reagent comprising a signal generating compound that generates a measurable signal prior to the performance of step (c).

16. The method of claim 14, wherein the mammal is selected from the group consisting of humans, cats, horses, and dogs.

17. A method of detecting antibodies specific for *A. phagocytophilum* comprising:
  contacting a test sample suspected of comprising antibodies specific for *A. phagocytophilum* with either (i) a polypeptide consisting essentially of SEQ ID NO:3, or (ii) the polypeptide consisting essentially of SEQ ID NO:3 and at least one of a polypeptide consisting essentially of SEQ ID NO:1 and SEQ ID NO:2, wherein the contacting is under conditions that allow polypeptide/antibody complexes to form;
  (b) detecting polypeptide/antibody complexes; wherein the detection of polypeptide/antibody complexes is an indication that antibodies specific for *A. phagocytophilum* are present in the test sample.

18. The method of claim 17, further comprising contacting the complexes of step (a) with an indicator reagent comprising a signal generating compound prior to the performance of step (b).

19. The method of claim 17, wherein the antibodies are fragments of antibodies.

20. The method of claim 17, wherein the amount of antibody in the test sample is determined.

21. The method of claim 17, wherein at least one of the polypeptides is in a multimeric form.

22. The method of claim 17 wherein the polypeptide consisting essentially of SEQ ID NO:3 and at least one of the polypeptides consisting essentially of SEQ ID NO:1 and SEQ ID NO:2 is a fusion protein comprising SEQ ID NO:3 and at least one of SEQ ID NO: 1 and SEQ ID NO: 2.

23. The method of claim 22 wherein at least one of the polypeptides of the fusion protein is in multimeric form.

* * * * *